(12) United States Patent
Tanaka

(10) Patent No.: US 9,089,592 B2
(45) Date of Patent: Jul. 28, 2015

(54) METHOD FOR MICRO-INCISION CATARACT SURGERY, A METHOD OF EVALUATION OF A VISCOELASTIC MATERIAL, A COMPOSITION FOR EVALUATION OF A VISCOELASTIC MATERIAL AND A METHOD FOR EVALUATION USING THE COMPOSITION

(75) Inventor: Takao Tanaka, Tokyo (JP)

(73) Assignees: SEIKAGAKU CORPORATION, Tokyo (JP); TOKYO MEDICAL UNIVERSITY, Tokyo (JP)

( * ) Notice: Subject to any disclaimer, the term of this patent is extended or adjusted under 35 U.S.C. 154(b) by 985 days.

(21) Appl. No.: 12/110,392

(22) Filed: Apr. 28, 2008

(65) Prior Publication Data

US 2008/0306024 A1  Dec. 11, 2008

Related U.S. Application Data

(60) Provisional application No. 60/924,002, filed on Apr. 26, 2007.

(51) Int. Cl.
*A61K 31/716* (2006.01)
*A61K 31/728* (2006.01)
*A61F 9/00* (2006.01)

(52) U.S. Cl.
CPC .............. *A61K 31/728* (2013.01); *A61F 9/0008* (2013.01)

(58) Field of Classification Search
CPC ..................................................... A61K 31/728
See application file for complete search history.

(56) References Cited

U.S. PATENT DOCUMENTS

| | | |
|---|---|---|
| 2002/0088233 A1 | 7/2002 | Ohnishi et al. |
| 2002/0183279 A1 | 12/2002 | Tanaka |
| 2009/0198213 A1 * | 8/2009 | Tanaka ......................... 604/506 |

FOREIGN PATENT DOCUMENTS

| | | |
|---|---|---|
| EP | 0 138 572 A2 | 4/1985 |
| WO | 92/18543 A1 | 10/1992 |

OTHER PUBLICATIONS

Fine et al., J Cataract Refract Surg "Power Modulations in New Phacoemulsification Technology", vol. 30, pp. 1014-1019 (2004).*
Bissen-Miyajima, H., J Cataract Refract Surg "Laboratory Science: In vitro behavior of ophthalmic viscosurgical devices during phacoemulsification", vol. 32, pp. 1026-1031 (2006).*
Sobaci et al., European Journal of Ophthalmology, "The effect of intraoperative antibiotics in irrigating solutions on aqueous humor contamination and endophthalmitis after phacoemulsification surgery", vol. 13, issue 9, pp. 773-778 (2003).*
George L. Spaeth, Ophthalmic Surgery: Principles and Practice, Third Edition, Elsevier Science, 2003, Chapter 9 "Nuclear Cracking Techniques"—Gaynor B. et al.*
"Phacoemulsification", also available at http://www.mondofacto.com/facts/dictionary?phacoemulsification; published Dec. 1998; last viewed Dec. 17, 2010.*
Miyata, K. et al., J Cataract Refract Surg, "Corneal endothelial cell protection during phacoemulsification", 2002, vol. 28, pp. 1557-1560.*
Miyata, H. et. al. "Clinical Comparison of Corneal Endothelium Cell Damage Using Hyaluronic Acids of Different Molecular Weights Following Cataract Surgery", IOL & RS, vol. 11, No. 4, pp. 266-269, Dec. 1997.

* cited by examiner

*Primary Examiner* — Shaojia Anna Jiang
*Assistant Examiner* — Bahar Craigo
(74) *Attorney, Agent, or Firm* — Sughrue Mion, PLLC

(57) ABSTRACT

A method for micro-incision cataract surgery, wherein a solution containing hyaluronic acid having a weight average molecular weight of from 600,000 to 1,200,000 or a salt thereof is injected into the anterior chamber, and flow rate of a perfusion liquid in the anterior chamber is set to about be 35 to 40 mL/min or less, a method for evaluating retentivity of a viscoelastic material, which uses a device consisting of a micro-flare ultrasonic chip arranged in water, a sleeve which covers said chip and a hollow cylinder into which said chip is inserted, and a composition for evaluation of retentivity of a viscoelastic material, which comprises at least said viscoelastic material and a fluorescent granule, are provided.

4 Claims, 4 Drawing Sheets

METHOD FOR MICRO-INCISION CATARACT SURGERY, A METHOD OF EVALUATION OF A VISCOELASTIC MATERIAL, A COMPOSITION FOR EVALUATION OF A VISCOELASTIC MATERIAL AND A METHOD FOR EVALUATION USING THE COMPOSITION

TECHNICAL FIELD

The present invention relates to a method for micro-incision cataract surgery which can suppress reduction of endothelial cells of cornea, a method of evaluation of retentivity of a viscoelastic material, an evaluation device to be used for this, a composition for evaluation of retentivity of a viscoelastic material, a method for evaluation using said composition, a micro-incision cataract surgery assisting agent to which these evaluation methods are applied, a method for screening an inhibitor of decrease of endothelial cells of cornea and the like.

BACKGROUND OF THE INVENTION

In recent years, micro-incision cataract surgery (to be also referred to as "MICS" hereinafter) has been broadly carried out since quick restoration of the eye after surgery is possible by it and can suppress generation of astigmatism.

The endothelial cell of cornea is an important cell relates to the transparency of the cornea. There is a possibility that the endothelial cells of cornea are decreased caused by an external wound or surgery on eyes or by the wearing of contact lenses. It is necessary to take care since they are cells which do not regenerate.

On the other hand, viscoelastic material such as hyaluronic acid, chondroitin sulfate, a salt thereof and hydroxypropylmethylcellulose is used as an intraocular tissue protective agent or space retentive substance in the ophthalmic surgery (cf. Patent References 1 and 2). Viscoelastic materials draw attention by cornea protecting effect thereof, and viscoelastic materials having proper molecular weight have been investigated from the viewpoint of therapeutic effect and inflammation properties (cf. Patent References 3 and 4).

[Patent Reference 1] US Patent Publication 2002/0183279 A1
[Patent Reference 2] US Patent Publication 2002/0088233 A1
[Patent Reference 3] European Patent Publication 0138572 A2
[Patent Reference 4] WO 92/18543

DISCLOSURE OF THE INVENTION

Problems Solved by the Invention

The inventors of the present invention have found that there are cases having high decreasing ratio of endothelial cells of cornea during postoperative period regardless of the absence of technical problems during the MICS operation. Thus, when the cause of the decrease of endothelial cells of cornea was investigated, it was revealed that it relates to the degree of difficulty such as the age of patient, nuclear hardness of crystalline lenses and the like. Additionally, it was revealed that difference in the molecular weight of simultaneously used viscoelastic materials is one of the causes. Namely, it was revealed that the decreasing ratio of endothelial cells of cornea is high when a high molecular weight viscoelastic material is used, and the decreasing ratio of endothelial cells of cornea is low when a low molecular weight viscoelastic material is used.

Accordingly, with the aim of preventing the decrease of endothelial cells of cornea by the MICS which uses a viscoelastic material, the present invention provides an MICS method having excellent movement and retentivity of a viscoelastic material under perfusion, a method of evaluation of movement and retentivity of the viscoelastic material, an evaluation device to be used for this, a composition for evaluation of movement and retentivity of the viscoelastic material, a method for evaluation using said composition, an MICS assisting agent to which these evaluation methods are applied, a method for screening an inhibitor of the decrease of endothelial cells of cornea and the like.

Means for Solving the Problems

As a result of conducting intensive studies, the inventors of the present invention have found that the above-mentioned objects can be achieved by employing the following constructions to accomplish the present invention.

Namely, the present invention is as follows:

(1) A method for micro-incision cataract surgery, wherein a solution containing hyaluronic acid having a weight average molecular weight of from 600,000 to 1,200,000 or a salt thereof is injected into the anterior chamber, and flow rate of a perfusion liquid in the anterior chamber is set to 45 mL/min or less (to be referred to as "a surgical method of the present invention" hereinafter);

(2) The method described in the above-mentioned (1), wherein concentration of the solution of hyaluronic acid or a salt thereof is about 1% (w/v);

(3) The method described in the above-mentioned (1) or (2), wherein the perfusion liquid contains antibiotics;

(4) A method for evaluating retentivity of a viscoelastic material by a device consisting of a micro-flare ultrasonic chip arranged in water, a sleeve which covers said chip and a cylinder in which said chip is arranged at an inlet side central part, which comprises a step of applying a viscoelastic material as the substance to be tested to the inner wall of said cylinder and subsequently let water flow from said sleeve at a flow rate of from 0 to 80 mL/min (to be referred to as "an evaluation method 1 of the present invention" hereinafter);

(5) The method for evaluation described in the above-mentioned (4), wherein the retentivity is a residual property, a stationary property or a stagnant property;

(6) A method for screening a micro-incision cataract surgery assisting agent, wherein the method described in the above-mentioned (4) is used (to be referred to as "a screening method 1 of the present invention" hereinafter);

(7) A method for screening an inhibitor of decrease of endothelial cells of cornea, wherein the method described in the above-mentioned (4) is used (to be referred to as "a screening method 2 of the present invention" hereinafter);

(8) A composition for evaluation of retentivity of a viscoelastic material, which comprises at least said viscoelastic material and a fluorescent pigment (to be referred to as "a composition of the present invention" hereinafter);

(9) A method for evaluating retentivity of a viscoelastic material contained in a composition, wherein said composition described in the above-mentioned (8) is used (to be referred to as "evaluation method 2 of the present invention" hereinafter);

(10) The method for evaluation described in the above-mentioned (9), wherein the retentivity is a residual property, a stationary property or a stagnant property;

(11) A method for screening a micro-incision cataract surgery assisting agent, wherein the method described in the above-mentioned (9) is used (to be referred to as "a screening method 3 of the present invention" hereinafter); and

(12) A method for screening an inhibitor of decrease of endothelial cells of cornea, characterized in that the method described in the above-mentioned (9) is used (to be referred to as "a screening method 4 of the present invention" hereinafter).

BEST MODE FOR CARRYING OUT THE INVENTION

The following describes the present invention in detail.
<1> Surgical Method of the Present Invention The surgical method of the present invention is a method for micro-incision cataract surgery, wherein a solution containing hyaluronic acid having a weight average molecular weight of from 600,000 to 1,200,000 or a salt thereof is injected into the anterior chamber, and flow rate of a perfusion liquid in the anterior chamber is set to be 45 mL/min or less.

The MICS is a surgical method of cataract, which comprises a step of incising cornea (size of the incised part is approximately 2 mm or less), cutting off anterior capsule, inserting a handpiece for ultrasonic aspiration, and crashing and sucking nucleus of the lens using ultrasonic wave under perfusion. At the time of this surgical operation, space in the anterior chamber can be kept and cornea and the like tissues can also be protected during the operation, by injecting a viscoelastic material into the anterior chamber.

One of the characteristics of the surgical method of the present invention is that a solution containing hyaluronic acid having a weight average molecular weight of from 600,000 to 1,200,000 or a salt thereof is used as the viscoelastic material in such MICS.

The salt of hyaluronic acid is not particularly limited as long as it is a medically acceptable salt. Examples of the salt of hyaluronic acid include alkali metal salts such as sodium salt and potassium salt and alkaline earth metal salts such as calcium salt and magnesium salt. Particularly, it is preferable to use a sodium salt (sodium hyaluronate).

As such a hyaluronic acid or a salt thereof, those which have a weight average molecular weight of within the range of from 600,000 to 1,200,000 can be used. Particularly, those having from 700,000 to 1,100,000 are more preferable, those having from 800,000 to 1,000,000 are more preferable and those having from 850,000 to 950,000 are more preferable.

Concentration of the solution containing hyaluronic acid or a salt thereof in the above-mentioned solution to be used in the surgical method of the present invention is not particularly limited as long as it is a concentration of within such a range that it can be used as the viscoelastic material for ophthalmic operation. Examples of the concentration include a concentration of from 0.6 to 145% (w/v). Particularly, from 0.7 to 1.4% (w/v) is preferable, from 0.8 to 1.3% (w/v) is more preferable, from 0.9 to 1.2% (w/v) is more preferable, about 1% (w/v) is more preferable, and 1% (w/v) is particularly preferable.

Also, volume of the solution containing hyaluronic acid or a salt thereof to be injected into the anterior chamber by the surgical method of the present invention is not particularly limited too, and can be appropriately decided by those skilled in the art according to individual patients.

Additionally, one of the characteristics of the surgical method of the present invention is that flow rate of a perfusion liquid in the anterior chamber by the MICS is set to be 45 mL/min or less. Although the flow rate is not particularly limited as long as it is within the range, from 45 mL/min to 20 mL/min is preferable, from 45 mL/min to 25 mL/min is preferable, from 45 mL/min to 30 mL/min is more preferable, and from 45 mL/min to 35 mL/min is particularly preferable.

In this connection, as the perfusion liquid to be used in the surgical method of the present invention, a commercially available article generally used in MICS can be used as such.

Additionally, according to the surgical method of present invention, antibiotics can be contained in the perfusion liquid. The antibiotics which can be contained in the perfusion liquid are not particularly limited too, examples of it include aminoglycoside antibiotics such as streptomycin, dihydrostreptomycin, dihydrodeoxystreptomycin, fradiomycin, neomycin, paromomycin, aminosidin, kanamycin, kanamycin B, tobramycin, dibekacin, amikacin, gentamicin, micronomicin, ribostamycin, bekanamycin and sisomicin, tetracycline antibiotics such as chlortetracycline, oxytetracycline, tetracycline, doxycycline and minocycline, chloramphenicol antibiotics such as chloramphenicol and thiamphenicol, macrolide antibiotics such as erythromycin, spiramycin, acetylspiramycin, midecamycin, leucomnycin, kitasamycin, josamycin and oleandomycin, lincomycin antibiotics such as lincomycin and clindamycin, penicillin antibiotics such as benzylpenicillin, phenoxymethylpenicillin, phenethicillin, propicillin, phenepenicillin, methicillin, oxacillin, cloxacillin, dicloxacillin, flucloxacillin, ampicillin, amoxicillin, ciclacillin, hetacillin, mecillinam, pivmecillinam, pivampicillin, talampicillin, bacampicillin, carbenicillin, carindacillin, carfecillin, ticarcillin, sulbenicillin, piperacillin, apalcillin and mezlocillin, cephein antibiotics, aztreonam such as cephalotin, cephaloridine, cefazolin, cefaloglycin, cephalexin, cefadroxil, cefatrizine, cefaclor, cefamandole, cefuroxime, cefotiam, cefoxitin, cefmetazole, cefsulodin, cefoperazone, ceftizoxime, cefotaxime, ceftazidime, cefixime, cefbuperazone, cefotetan, cefminox, latamoxef and flomoxef, monobactam antibiotics such as aztreonam and carumonam, antibiotics such as nystatin, amphotericin B, trichomycin, pimaricin, griseofulvin, flucytosine, clotrimazole, miconazole, econazole, isoconazole, ketoconazole, fluconazole and itraconazole, sulfa drugs such as sulfathiazole, sulfamethizole, sulfisomidine, sulfamethoxazole, sulfamethoxypyrimidine, sulfamethoxin, sulfaphenazole, sulfamonomethoxin, sulfaphenazole, sulfisoxazole and sulfamonomethoxin, sulfone drugs such as 4,4'-diaminodiphenylsulfonate, glucosulfone sodium, sulfoxone sodium and thiazole sulfone, antituberculous drugs such as para-aminosalicylic acid, isoniazid, ethionamide, polothionamide and ethambutol, quinolone antibiotics such as nalidixic acid, pipemidic acid, ofloxacin, norfloxacin, enoxacin, ciprofloxacin, tosufloxacin, levofloxacin and parfloxacin, nitrofuran compounds such as nitrofurantoin, furazolidone, nifuratel, nifuradene, nitrofurazone and nifuroxime, dihydrofolate reductase inhibitors such as trimethoprim and pyrimethamine, and cycloserine, fosfomycin, bacitracin, vancomycin, viomycin, capreomycin, fusidic acid, rifampicin, polymyxin B, colistin and gramicidin S.

According to the surgical method of the present invention, by using a solution containing the above-mentioned specific hyaluronic acid or a salt thereof as a viscoelastic material and adopting the above-mentioned specific flow rate of a perfusion liquid in MICS as described in the above, it can be realized a movement in which said viscoelastic material is torn into small pieces (slender pieces) and gradually carried away under perfusion as is described later, so that the endothelial cells of cornea can be protected at a further higher level.

<2> Evaluation Method 1 of the Present Invention

The evaluation method 1 of the present invention is a method for evaluating retentivity of a viscoelastic material by a device consisting of a micro-flare ultrasonic chip arranged in water, a sleeve which covers said chip and a cylinder in which said chip is arranged at an inlet side central part, which comprises a step of applying a viscoelastic material as the substance to be tested to the inner wall of said cylinder and subsequently let water flow from said sleeve at a flow rate of from 0 to 80 mL/min.

An embodiment of the device to be used in the evaluation method 1 of the present invention, namely a device consisting of a micro-flare ultrasonic chip (a sleeve is attached thereto) and a cylinder in which said chip is arranged at an inlet side central part, is shown in FIG. 1. The left side structure of the arrow shown in FIG. 1 is the micro-flare ultrasonic chip (a sleeve is attached thereto). Also, the innermost cylinder shown in the right side of the same arrow is the "cylinder" of the above-mentioned device. In this connection, the cylinder which is surrounding outside of said cylinder and the rectangular parallelepiped structure positioned at the bottom thereof are merely structures for fixing the cylinder of the above-mentioned device (the innermost cylinder shown in FIG. 1). Accordingly, said cylinder may be fixed by a structure other than this.

In FIG. 1, the micro-flare ultrasonic chip (a sleeve is attached thereto) is shifted the arrow direction and finally arranged at an inlet side central part of the cylinder (the innermost cylinder). An embodiment after this arrangement is shown in FIG. 2.

As both of the micro-flare ultrasonic chip and the sleeve to be attached to said tip, which are used in the evaluation method 1 of the present invention (and the above-mentioned device), those which are on the market for MICS use can be used as such.

Examples of the sleeve include Micro-sleeve, Ultra-sleeve, Nano-sleeve and the like, and it is preferable to use a sleeve for micro-incision surgery (Ultra-sleeve or Nano-sleeve).

Also, although the cylinder (the innermost cylinder in FIG. 1) which is used in the evaluation method 1 of the present invention (and the above-mentioned device) is not limited too, a transparent cylinder is preferable since movement of the viscoelastic material to be applied to the inside can be observed from the outside. Also, although its material is not particularly limited too, an acrylic product is preferable. Additionally, regarding the size of the cylinder, a cylinder having such a small size that the current of perfusion liquid generated from the sleeve contacts with the viscoelastic material to be applied to the inside of the cylinder may be used. Specifically, examples of it include a cylinder having an inner diameter of approximately from 5 mm to 15 mm, preferably approximately from 6 mm to 10 mm.

The above-mentioned device is arranged in a water tank filled with such a volume of aqueous solution such as water or physiological saline that at least the above-mentioned cylinder is completely submerged.

In the evaluation method 1 of the present invention, firstly, the viscoelastic material is applied to the inside (inner wall) of the cylinder of the above-mentioned device. An image at the time of this application is shown in FIG. 3. In this connection, the viscoelastic material as the substance to be tested may be applied under such a state that the micro-flare ultrasonic chip (a sleeve is attached thereto) is arranged at an inlet side central part or, as a matter of course, may be applied under unarranged state, subsequently arranging said chip at an inlet side central part FIG. 3 shows an applied state under which the chip is not arranged at a predetermined position.

Volume of the viscoelastic material to be applied (substance to be tested) can be optionally set by those skilled in the art depending on the size and the like of the cylinder to be used. When a cylinder having the aforementioned size is used for example, examples of the volume include approximately from 0.1 mL to 0.2 mL.

Also, the application method is not particularly limited too, as long as it can form a state in which the viscoelastic material (substance to be tested) is adhered to the inner wall of the cylinder. Examples of the method include a method in which the viscoelastic material (substance to be tested) is coated on the inner wall of the cylinder.

Thereafter, the retentivity is evaluated by observing the sate of the viscoelastic material (substance to be tested) being carried away by the perfusion liquid gushed out from the sleeve arranged at an inlet side central part of the cylinder (see FIG. 2. However, the viscoelastic material (substance to be tested) applied to the inner wall of the cylinder is not shown in FIG. 2).

The term retentivity as used herein may be any one of the residual property, stationary property and stagnant property.

Flow rate of the perfusion liquid to be gushed out from the sleeve can be appropriately set by those skilled in the art according to the purpose of the retentivity evaluation of the viscoelastic material (substance to be tested). Specifically, examples of the flow rate is from 0 to 80 mL/min.

For example, when the flow rate of said perfusion liquid is set to be approximately 45 mL/min or less, for example from 45 mL/min to 20 mL/min, particularly from 45 mL/min to 25 mL/min, particularly from 45 mL/min to 30 mL/min, particularly from 45 mL/min to 35 mL/min, it is almost the same as the flow rate of perfusion liquid in MICS, so that the action (retentivity) of the viscoelastic material (substance to be tested) in the MICS can be reproduced.

By this, retentivity of the applied viscoelastic material (substance to be tested), such as requirement for a certain period of time during which the material is carried away by forming masses after commencement of perfusion (upper side of FIG. 4) or is torn into small pieces (slender pieces) and gradually carried away (lower side of FIG. 4) and finally completely carried away, can be evaluated. In this connection, although it is not shown in FIG. 4, there is a case in which the applied entire viscoelastic material (substance to be tested) is carried away in a lump.

<3> Screening Methods 1 and 2 of the Present Invention

The screening method 1 of the present invention is a method for screening a micro-incision cataract surgery assisting agent, wherein the evaluation method 1 of the present invention is used.

The screening method 2 of the present invention is a method for screening an inhibitor of decrease of endothelial cells of cornea, wherein the evaluation method 1 of the present invention is used.

In both of the screening methods, when a viscoelastic material (substance to be tested) is torn into small pieces (slender pieces) and gradually carried away in the evaluation method 1 of the present invention, said viscoelastic material (substance to be tested) can be selected as a candidate substance of the micro-incision cataract surgery assisting agent or inhibitor of decrease of endothelial cells of cornea, which can protect endothelial cells of cornea at a high level.

It is desirable that flow rate of the perfusion liquid to be used in these screening methods is approximately 45 mL/min or less, for example from 45 mL/min to 20 mL/min, particularly from 45 mL/min to 25 mL/min, particularly from 45 mL/min to 30 mL/min, particularly from 45 mL/min to 35 mL/min.

<4> Composition of the Present Invention, Evaluation Method 2 of the Present Invention, Screening Methods 3 and 4 of the Present Invention The composition of the present invention is a composition for evaluation of retentivity of a viscoelastic material, which comprises at least said viscoelastic material and a fluorescent pigment.

The term "viscoelastic material" as used herein means an aqueous solution having viscoelasticity, which is used for keeping the space in the anterior chamber and protecting corneal tissue during ophthalmic surgery. Specifically, examples of it include hyaluronic acid, chondroitin sulfate, or salts thereof or a mixed solution thereof and hydroxypropylmethylcellulose.

Additionally, the fluorescent pigment which can be used herein is not particularly limited too, as long as it can be dissolved or suspended in the viscoelastic material, and can be appropriately selected by those skilled in the art. By the use of the composition of the present invention, evaluation of retentivity of the viscoelastic material contained in said composition can be carried out with markedly good visibility.

The evaluation method 2 of the present invention is a method for evaluating retentivity of a viscoelastic material contained in a composition, wherein said composition is used. Additionally, the screening methods 3 and 4 are a method for screening a micro-incision cataract surgery assisting agent and a method for screening an inhibitor of decrease of endothelial cells of cornea, wherein the evaluation method 2 of the present invention is used.

The evaluation method 2 of the present invention can be carried out using the composition of the present invention, for example in accordance with the evaluation method 1 of the present invention. Also, the screening method 3 of the present invention can be carried out using the composition of the present invention, for example in accordance with the screening method 1 of the present invention. Additionally, the screening method 4 of the present invention can be carried out using the composition of the present invention, for example in accordance with the screening method 2 of the present invention.

Although the following describes the present invention in detail with reference to examples, the present invention is not limited thereto.

Example 1

In the cases of aging cataract in which MICS was carried out using viscoelastic materials, 187 eyes of humans who completed MICS without complications during the surgery were used as the objects and the clinical data and postoperative decreasing ratio of endothelial cells of cornea were studied. As a result, the decreasing ratio of endothelial cells of cornea was 8.2±8.7% (average value±SD) and its median was 6%. However, all of the cases in which the values of decreasing ratio of endothelial cells of cornea showed minus values (increase of endothelial cells of cornea) were regarded as 0% for reasons of calculation.

Next, individual cases contained in the all cases were divided into two groups bordering the median (6%), namely a group in which the decreasing ratio of endothelial cells of cornea was 6% or more (94 eyes; to be referred to as "high value group" hereinafter) and a group in which the decreasing ratio of endothelial cells of cornea was less than 6% (93 eyes; to be referred to as "low value group" hereinafter), and the background factors were compared and examined. As a result, it was revealed that the occupying ratio of the cases which used a high molecular weight viscoelastic material (phosphate buffered saline containing 1% (w/v) of sodium hyaluronate having a weight average molecular weight of from 1,900,000 to 3,900,000) was high in the high value group, and the occupying ratio of the cases which used a low molecular weight viscoelastic material (phosphate buffered saline containing 1% (w/v) of sodium hyaluronate having a weight average molecular weight of from 600,000 to 1,200,000) was significantly high in the low value group.

The result is shown in Table 1.

TABLE 1

| | Decreasing ratio of endothelial cell of cornea | | |
|---|---|---|---|
| | Low value group | High value group | Total |
| High molecular weight viscoelastic material (average molecular weight 1,900,000 to 3,900,000) | 51 eyes | 65 eyes | 116 eyes |
| Low molecular weight viscoelastic material (average molecular weight 600,000 to 1,200,000) | 42 eyes | 29 eyes | 71 eyes |

$P = 0.041$ ($\chi^2$ test), $P = 0.038$ (Fisher test)

Example 2

An acrylic transparent cylinder having an outer diameter of 10 mm and an inner diameter of 8 mm was arranged in a water tank in parallel with the ground and fixed thereto. Additionally, a micro-flare ultrasonic chip (manufactured by Alcon) was mounted on a handpiece for ultrasonic aspiration, and this was arranged at an inlet side central part of the above-mentioned cylinder in parallel with the ground and fixed thereto.

The measurement was carried out by mounting a Micro-sleeve, Ultra-sleeve or Nano-sleeve on the above-mentioned ultrasonic chip. In this connection, the water tank was filled with such a volume of physiological saline that at least the above-mentioned cylinder was completely submerged.

Next, about 0.15 g of a commercially available fluorescent pigment was mixed with each of various viscoelastic materials, and about 0.1 mL portion thereof was coated on the inlet inner wall of the cylinder.

Subsequently, a bottle of physiological saline (perfusion liquid) was arranged at a 65 cm-higher position from the aforementioned ultrasonic chip, said perfusion liquid was introduced from it to the ultrasonic chip mounted with the aforementioned Micro-sleeve. The perfusion liquid was gushed out into the aforementioned cylinder through a hole arranged on the Micro-sleeve. Flow rate of the perfusion liquid was 78 mL/min in average when the Micro-sleeve was mounted, 42 mL/min in average when the Ultra-sleeve was mounted and 35 mL/min in average when the Nano-sleeve was mounted (p=0.004).

Movement of the viscoelastic material coated on the inner wall of the aforementioned cylinder caused by the perfusion was video photographed and observed.

In this connection, the viscoelastic material used in the study was phosphate buffered saline containing 1% (w/v) of sodium hyaluronate having (A) a weight average of 500,000, (B) a weight average of from 900,000 to 1,200,000 or (C) a weight average of from 1,900,000 to 3,900,000.

As a result, when the Micro-sleeve was used, each of the viscoelastic materials of the aforementioned (B) and (C) was carried away in a lump after about 2 seconds in average of the commencement of perfusion.

When the Ultra-sleeve or Nano-sleeve was used, the viscoelastic material of the aforementioned (C) was carried away in a lump after about 2 to 4 seconds. On the other hand, the viscoelastic material of the aforementioned (B) was torn into small pieces (slender pieces) and gradually carried away, and 10 seconds or more were required until all of them were finally carried away.

The viscoelastic material of the aforementioned (A) was not carried away by the perfusion but remained on the wall by the use of any one of the sleeves.

Based on these results, it was considered that when a sleeve for micro-incision surgery (Ultra-sleeve or Nano-sleeve) is used, depending on the kind of viscoelastic material, its viscosity partly changes accompanied by the lowering of flow rate. Therefore, its intraocular retentivity can be different from the case of using Micro-sleeve.

Example 3

The above-mentioned (B) or (C) as the viscoelastic material (each of them was prepared by mixing with a fluorescent pigment similarly as the case of Example 2) was injected into pig's eyes, a trial micro-incision surgery was carried out using a Micro-sleeve, Ultra-sleeve or Nano-sleeve, and movement of said viscoelastic material was video-photographed and observed.

As a result, each of the viscoelastic materials of the aforementioned (B) and (C) was carried away in a lump after the commencement of perfusion when the Micro-sleeve was used. When the Ultra-sleeve or Nano-sleeve was used, the viscoelastic material of the aforementioned (C) was carried away in a lump after the commencement of perfusion. On the other hand, the viscoelastic material of the aforementioned (B) was torn into small pieces (slender pieces) and gradually carried away, and a certain period of time was required until all of them were finally carried away.

It was shown based on the results of Example 1 and the results of movement of viscoelastic materials in Example 3 that it is preferable to use a viscoelastic material having a weight average molecular weight of from 900,000 to 1,200,000, from the viewpoint of protecting endothelial cell of cornea, when the Ultra-sleeve or Nano-sleeve (flow rate of the perfusion liquid is approximately from 35 to 40 mL/min) is used. It was shown that when such a viscoelastic material is used, damage on the endothelial cell of cornea also becomes small, since the viscoelastic material contacting with the endothelial cell of cornea is torn into small pieces (slender pieces) and gradually carried away without being carried away as a lump at a stretch under the perfusion (it is highly possible that endothelial cell of cornea is also peeled off at a stretch by this).

Additionally, since the results of Example 2 and the results of Example 3 were markedly correlated, it was shown also that a viscoelastic material suitable for protecting the endothelial cell of cornea can be screened by selecting a viscoelastic material which is torn into small pieces (slender pieces) and gradually carried away under perfusion, using the device described in Example 2.

From the above results, it was suggested that a low molecular weight viscoelastic material shows a movement which was torn into small pieces (slender pieces) and gradually carried away by the perfusion liquid when an Ultra-sleeve or Nano-sleeve is used in the MICS. Damage on the endothelial cell of cornea can be suppressed thereby.

Figure 1:
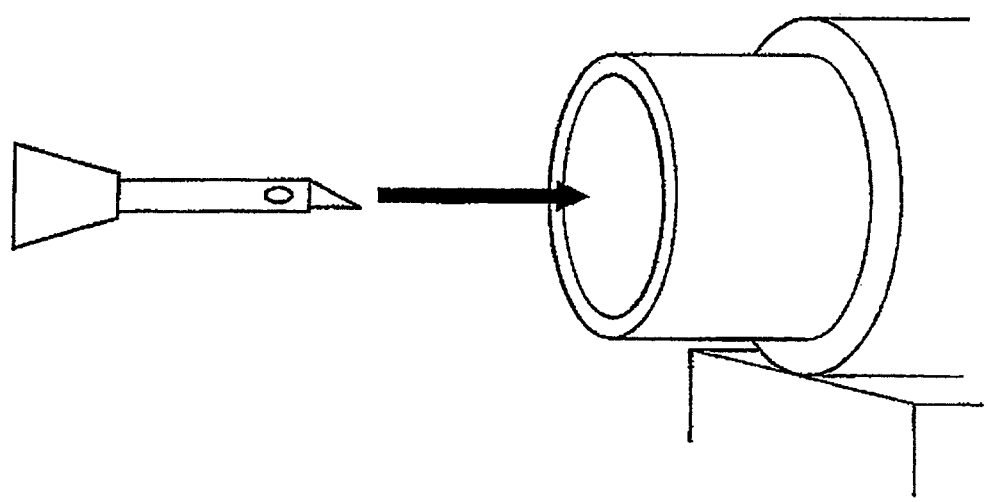
FIG. 1 shows an embodiment of the device for evaluating viscoelastic materials.
Figure 2:
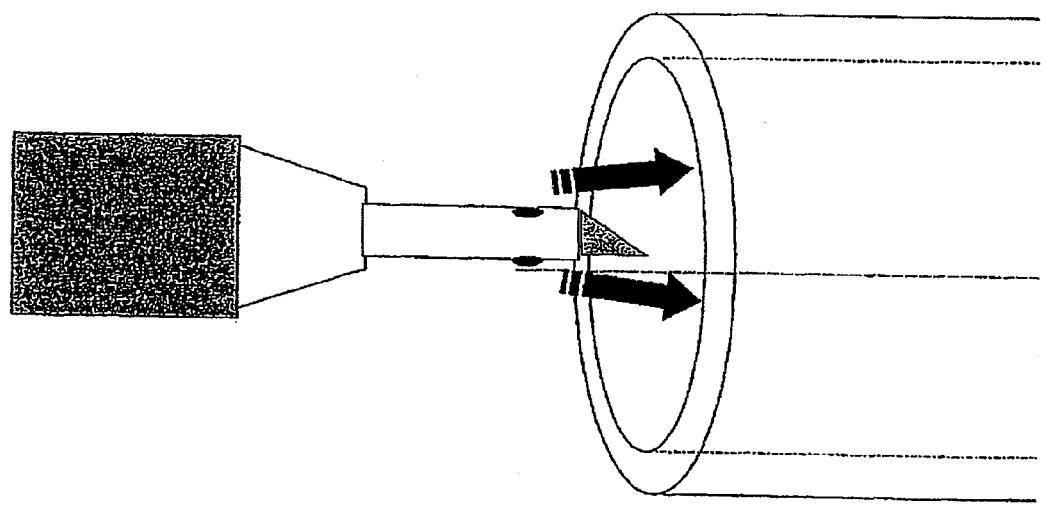
FIG. 2 shows an embodiment after arrangement of a micro-flare ultrasonic chip (a sleeve is attached thereto) at an inlet side central part of the cylinder.
Figure 3:
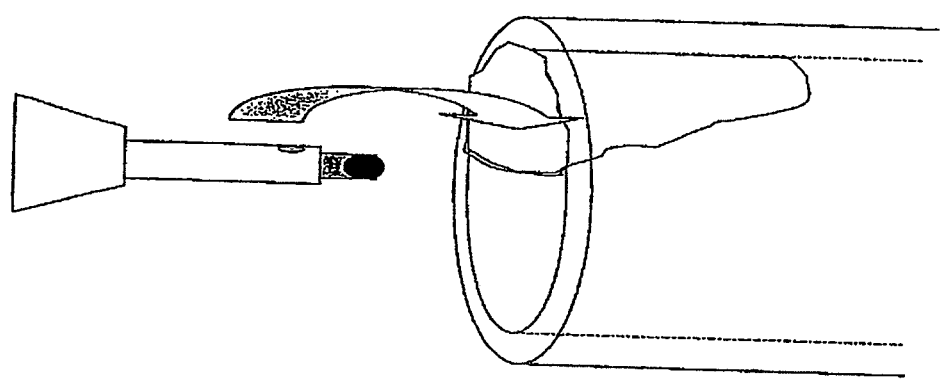
FIG. 3 shows an image when a viscoelastic material is applied to the inside (inner wall) of the cylinder of the above-mentioned device.
Figure 4:
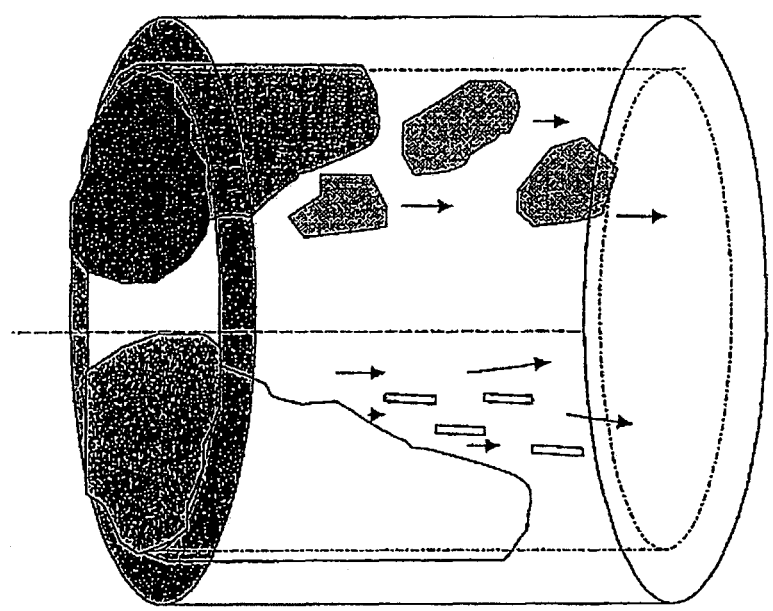
FIG. 4 shows a schematic illustration of a state in which the applied viscoelastic material (substance to be tested) is carried away by forming masses (upper half of the drawing) or is torn into small pieces (slender pieces) and gradually carried away (lower half of the drawing).

The invention claimed is:

1. A method for tearing a viscoelastic material into smaller-sized pieces and gradually carrying away the smaller-sized pieces under perfusion in micro-incision cataract surgery comprising incising cornea, injecting the viscoelastic material into the anterior chamber through the incision, crashing nucleus of the lens using ultrasonic wave and removing the crashed nucleus under perfusion of a perfusion fluid using an Ultra-sleeve or Nano-sleeve, wherein the viscoelastic material is a solution consisting of hyaluronic acid having a weight average molecular weight of from 600,000 to 1,200,000 or salt thereof and a saline solution to dissolve the hyaluronic acid or salt thereof, concentration of the hyaluronic acid or salt thereof in the solution is about 1% (w/v), and flow rate of the perfusion fluid in the anterior chamber is set to be 30 to 45 mL/min, wherein the viscoelastic material is torn into smaller-sized pieces and gradually carried away under perfusion.

2. The method according to claim 1, wherein the perfusion fluid contains antibiotics.

3. The method according to claim 1, wherein the weight average molecular weight of hyaluronic acid is from 850,000 to 950,000.

4. The method according to claim 1, wherein the flow rate of the perfusion fluid is 35 mL/min to 45 mL/min.

* * * * *